(12) United States Patent
Rogers et al.

(10) Patent No.: US 10,319,467 B2
(45) Date of Patent: Jun. 11, 2019

(54) MEDICAL INFORMATION NAVIGATION ENGINE (MINE) SYSTEM

(71) Applicants: Robert Derward Rogers, Pleasanton, CA (US); Shahram Shawn Dastmalchi, San Ramon, CA (US); Darren Matthew Schulte, San Francisco, CA (US); Imran N. Chaudhri, Potomac, MD (US); Mary Ellen Campana, San Mateo, CA (US); Vishnuvyas Sethumadhavan, Mountain View, CA (US)

(72) Inventors: Robert Derward Rogers, Pleasanton, CA (US); Shahram Shawn Dastmalchi, San Ramon, CA (US); Darren Matthew Schulte, San Francisco, CA (US); Imran N. Chaudhri, Potomac, MD (US); Mary Ellen Campana, San Mateo, CA (US); Vishnuvyas Sethumadhavan, Mountain View, CA (US)

(73) Assignee: APIXIO, INC., San Mateo, CA (US)

( * ) Notice: Subject to any disclaimer, the term of this patent is extended or adjusted under 35 U.S.C. 154(b) by 495 days.

(21) Appl. No.: 13/964,031

(22) Filed: Aug. 9, 2013

(65) Prior Publication Data
US 2014/0046697 A1 Feb. 13, 2014

Related U.S. Application Data

(63) Continuation-in-part of application No. 13/223,228, filed on Aug. 31, 2011, now Pat. No. 10,176,541.
(Continued)

(51) Int. Cl.
*G06Q 50/24* (2012.01)
*G16H 10/60* (2018.01)
*G16H 40/20* (2018.01)

(52) U.S. Cl.
CPC ............ *G16H 10/60* (2018.01); *G06Q 50/24* (2013.01); *G16H 40/20* (2018.01)

(58) Field of Classification Search
None
See application file for complete search history.

(56) References Cited

U.S. PATENT DOCUMENTS

| 5,544,044 A | * | 8/1996 | Leatherman | G06F 19/324 705/3 |
| 2002/0120466 A1 | * | 8/2002 | Finn | G06F 19/328 705/2 |

(Continued)

FOREIGN PATENT DOCUMENTS

KR 10-2012-0004749 1/2012

OTHER PUBLICATIONS

Bentkus et al., "Confidence Bounds for a Parameter" Sep. 2001 Mathematics Subject Classification.*
(Continued)

*Primary Examiner* — Neal Sereboff
(74) *Attorney, Agent, or Firm* — Kang S. Lim

(57) ABSTRACT

A medical information navigation engine (MINE) for transacting medical information by receiving medical information from a medical sources, identifying, mapping, and consolidating the received medical information by a back-end medical processor, presenting access to specific relevant data, based on a user's security privileges, within the identified, mapped, and consolidated medical information, based on user-specific functions or roles by a front-end medical processor, and generating user-customized processed medi-
(Continued)

cal information to a plurality of users, with at least a portion of the user-customize processed medical information being provided to each of the plurality of users based on its relevancy to each user's specific function or role and each user's associated security privileges.

10 Claims, 4 Drawing Sheets

Related U.S. Application Data

(60) Provisional application No. 61/682,217, filed on Aug. 11, 2012, provisional application No. 61/379,228, filed on Sep. 1, 2010.

(56) References Cited

U.S. PATENT DOCUMENTS

| | | | |
|---|---|---|---|
| 2003/0084043 A1* | 5/2003 | Acharya | G06F 16/2462 |
| 2004/0172297 A1 | 9/2004 | Rao et al. | |
| 2005/0240439 A1* | 10/2005 | Covit | G06Q 10/00 705/2 |
| 2007/0055552 A1 | 3/2007 | Clair et al. | |
| 2008/0052255 A1* | 2/2008 | Fan | G06N 20/00 706/12 |
| 2010/0131438 A1 | 5/2010 | Pandya et al. | |
| 2011/0093293 A1* | 4/2011 | G. N. | G06Q 10/06 705/3 |
| 2011/0119089 A1 | 5/2011 | Carlisle | |
| 2012/0060216 A1* | 3/2012 | Chaudhri | G06Q 50/22 726/21 |
| 2012/0278102 A1* | 11/2012 | Johnson | G06Q 10/10 705/3 |
| 2013/0046529 A1* | 2/2013 | Grain | G06F 17/289 704/2 |
| 2013/0124523 A1* | 5/2013 | Rogers | G06F 19/32 707/737 |
| 2013/0332194 A1* | 12/2013 | D'Auria | G16H 10/60 705/3 |

OTHER PUBLICATIONS

Korean Intellectual Property Office, ISA, "International Search Report and Written Opinion" in PCT Application No. PCT/US2013/054440, dated Dec. 2, 2013, 10 pages.

* cited by examiner

MEDICAL INFORMATION NAVIGATION ENGINE (MINE) SYSTEM

CROSS REFERENCE TO RELATED APPLICATION

This non-provisional application claims the benefit of provisional application No. 61/682,217 filed on Aug. 11, 2012, entitled "Medical Information Navigation Engine (MINE) System", which application is incorporated herein in its entirety by this reference. This application is also a continuation-in-part application which claims the benefit of application Ser. No. 13/223,228 filed on Aug. 31, 2011, entitled "Medical Information Navigation Engine (MINE) System", which application claims priority to U.S. Provisional Application No. 61/379,228 filed on Sep. 1, 2010, of the same title, both applications are incorporated herein in their entirety by this reference.

BACKGROUND

The present invention relates to medical information engine, and particularly to management and consolidation of medical information.

Despite rapid growth of innovation in other fields in recent decades, the world of medical information, including patient medical records, billing, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

Currently, when a patient sees various medical professionals over the years, there is no method for universally tracking recommendations, thoughts, prescriptions, diagnosis. This hinders the job of insurance companies in making certain requisite determinations, physicians making decisions that directly impact the health of the patient, and hospitals and other medical institutions who similarly rely but do not have the benefit of the requisite information, not to mention the patient.

Further, there are problems in the current medical system that are associated with patient identity in that due to the exposure of a patient to various medical associations/professionals over the years and the possibility of various ways of identifying the same patient, patients' records and identity are oftentimes compromised, creating a slew of problems both for the patient as well as those treating the patient.

Further, privacy of a patient's health records is not currently reliably maintained, as there are too many cases of health record compromises. Additionally, patient control of access to medical information is nearly nonexistent. Additionally, secure and remote access of medical information is currently lacking.

Therefore, what is needed is a method and apparatus for managing medical information in a manner that is beneficial, reliable, portable, flexible, and efficiently usable to those in the medical field, including patients.

SUMMARY

To achieve the foregoing in accordance with the present invention, to overcome the limitations in the prior art described above, and to overcome other limitations that will become apparent upon reading and understanding the present specification, the present invention discloses a method and a corresponding structure for transacting medical information.

Briefly, a method of transacting medical information is disclosed to include receiving medical information from a medical sources, identifying, mapping, and consolidating the received medical information by a back-end medical processor, presenting access to specific relevant data, based on a user's security privileges, within the identified, mapped, and consolidated medical information, based on user-specific functions or roles by a front-end medical processor, and generating user-customized processed medical information to a plurality of users, with at least a portion of the user-customize processed medical information being provided to each of the plurality of users based on its relevancy to each user's specific function or role and each user's associated security privileges.

These and other objects and advantages of the invention will no doubt become apparent to those skilled in the art after having read the following detailed description of the preferred embodiments illustrated in the several figures of the drawing. Note that the various features described above may be practiced alone or in combination. These and other features will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Figure 1:
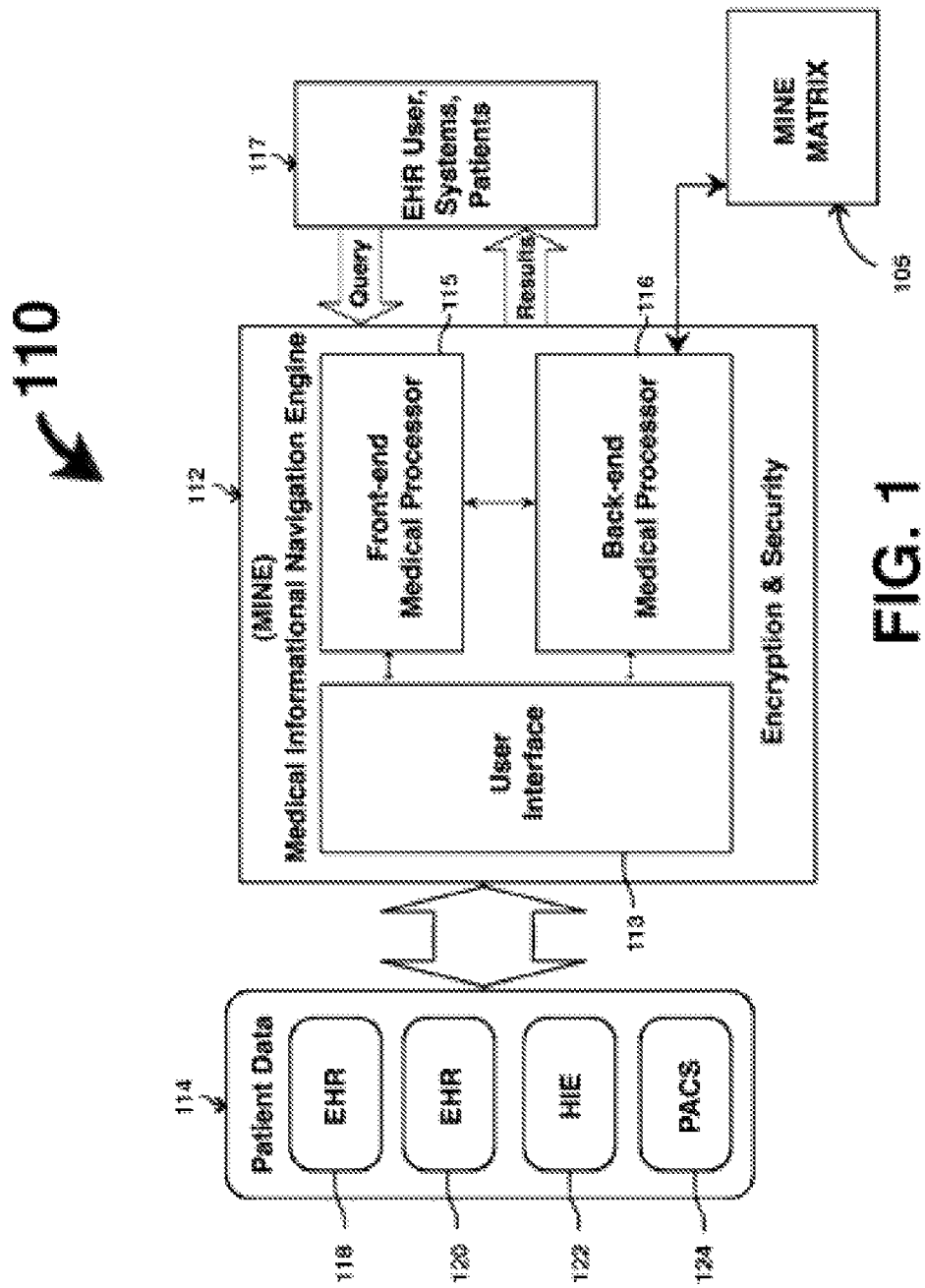
FIG. 1 shows a medical system 110 including a medical information navigation engine (MINE) 112, in accordance with one embodiment of the invention.

Referring now to FIG. 1, medical system 110, in accordance with an embodiment of the invention. The system 110 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124. The MINE 112 is shown to include interface 113, a backend medical processor 116, and a front-end medical processor 115. Depending on the implementation, processors 115, 116 can be distributed, e.g., using cloud computing. Processors 115, 116 can also be combined.

"Medical information", as used herein, refers to any health-related information, including but not limited to patient medical records, patient entered information, care team entered information, healthcare device generated information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents.

The information in the MINE 112 is encrypted and secure to ensure privacy of sensitive medical information.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and deduplication, generally refers to removing of redundant patient medical records, such as, multiple records for the same individual appearing as though the records are for different individuals or multiple data elements that are recorded similarly but slightly differently in the different sources. In this case, the processor 16 recognizes that the records belong to a single individual or are the same data and just recorded differently and automatically consolidates them. The patient or a user of the system 110 may also manually perform reconciliation. Whether or not reconciliation is performed is advantageously determined by the processor 116.

The processor 116 outputs the indexed, tagged and reconciled information to the processor 115. The foregoing tasks are a generalization and further details of each are provided below.

The processor 115 performs certain tasks on the information provided by the interface 113 and the processor 116, which include query, search, presentation, and quality checking. The output of the processor 115 is the output of the MINE 112, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g., the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. Information, uploaded to the MINE 112, by users, such as output 114, in some embodiments, is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that general practitioner Dr. Smith's new patient, Joan Sample, has a complaint of chest pain. Joan has brought several ACCDs and a 600-page pdf file of her chart. She has seen a cardiologist who uses NextGen and a G.I. specialist whose charts are in a e-MDs, and has visited the emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112 (examples of such screens are shown in subsequent figures herein). He is presented with relevant lab results, such as CKMB and Amulase, relevant diagnostic results, such as EKG and chest CT scan, and all progress notes and consult reports in which concepts relevant to chest pain, like "GERD" and "Holter monitor", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to a chest CT scan. Accordingly and advantageously, the Lexical and Medical concept search solves Dr. Smiths' information overload problem by returning information in the chart most relevant to Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, and consolidating by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

While Healthcare organizations today are struggling with use of greater volumes of digitized patient data stored in various formats across disparate systems. Most data created in clinical applications is textual and not computable by information systems. The inability to efficiently retrieve knowledge not only limits efforts to improve patient safety and outcomes, but also leads to missed quality and financial objectives.

In accordance with one embodiment of the present invention, a system 110 can integrate and intelligently analyze structured and unstructured information that resides across a healthcare organization. MINE 112 includes a virtual Health Information Exchange (HIE) platform and Clinical Knowledge Exchange™ (CKX) CKXREF, thereby enabling healthcare organizations to fill the knowledge gaps created by disparate and poorly connected computer systems and clinical information largely represented in textual form. MINE 112 also provides Semantic Tagging and Reconciling of an integrated patient data set by the CKX CKXREF to make information accessible and actionable by clinical, administrative and financial systems.

In some embodiments, Data access and analytics modules enabling organizations to improve the quality of patient care while lowering costs and optimizing reimbursements, including modules such as a Patient Analyzer, a Population Analyzer, a Quality Optimizer, and a HCC Optimizer.

The CKX platform CKXREF and its modules can be web-based, thereby reducing IT operations overhead for managing servers and simplifying account activation and user administration processes.

Core Technology

MINE 112 (Medical Information Navigation Engine) offers a technology solution to the information overload problem by presenting a unique interface to both structured and unstructured data.

The proliferation of electronic health records among providers, and government initiatives like meaningful use, have caused explosive growth in the volume of clinical data. Large amounts of both structured data, such as coded lab tests and procedures; and unstructured data, such as encounter notes and transcriptions is available to providers. Solutions for meaningful ways of navigating the data and preventing information overload are critical for health care providers to enhance care quality.

MINE 112 enables providers to enter free text queries as they would with any search engine and returns medically relevant results across both structured data and unstructured data. Using advanced natural language processing (NLP) technology to understand the intent behind the queries typed by the user, MINE 112 is able to return the most relevant results to that query.

As an example, a general practitioner (GP) has a new patient, John Doe complaining of chest pain and palpitations. John has a complicated medical history with various labs, medications and procedures recorded over many years. As soon as the doctor begins typing his query, MINE 112 uses finite state transducer technology xref to understand that chest pain is a medical concept and is able to suggest possible completions.

Once the GP completes his query and presses the search button, MINE 112 uses its Semantic Query Processing Engine capable of understanding medical language to tag medical concepts in the query.

Using such tagged information, MINE 112 is able to search both the textual content and structured information present in the patient's history by using MATRIX 105 (Medical Application Terminology Relation IndeX), a proprietary knowledge base of medical concepts and the semantic relations between them. Note that MATRIX 105 can be external or internal with respect to MINE 112, or combinations thereof.

For example, in the query "chest pain with palpitations", the terms "chest pain" and "palpitations" are automatically tagged with concepts from MATRIX 105.

In some embodiments, MATRIX 105 knowledge base can include approximately four or more million primary medical concepts and tens of millions of relationships between the concepts. This extensive knowledge base can be constructed by a combination of various techniques. For example, many of the commonly used clinical terminologies like ICD-9, CPT, and LOINC have been integrated into MATRIX 105. Further, content from a variety of large medical corpora like medical references and text from medical encounters is processed extract medical knowledge. Additional concepts, abbreviations and synonyms are identified in this way. NLP technologies such as named entity recognition (NER) are used to recognize various medically relevant concepts within the text. This processed text is passed through a Statistical Semantic Analysis Engine ENGINEREF which has been optimized to predict the strength of relationship between two medical concepts. This combination of pre-existing terminologies and new relationships mined from medical corpora creates a knowledge base that drives a Search Engine of MINE 112 to return the most relevant structured data and unstructured content in response to any free text query.

The deep integration of MINE 112 with the MATRIX 105 knowledge base filters out irrelevant structured data—and presents a care provider with the information most relevant to his needs. In this example, the GP will see that unrelated problems are filtered out—and only the problems that might be related to the complaint are highlighted. Because of the MATRIX 105 knowledge base, MINE 112 is able to highlight "shoulder pain" because it is strongly related to chest pain. MINE 112 is also able to perform similar highlighting for lab tests and procedures.

Apart from providing sophisticated concept based search on structured data, MINE 112 uses state of the art indexing and search technologies to provide semantic searching capabilities for textual content found in encounter notes. MINE 112 understands medical concepts and knows to search for "chest pain", and also for its synonyms such as "chest pressure" and "chest discomfort". MINE 112 can display easy-to-scan snippets for each medical concept found in the text, giving the health care provider immediate access to relevant information.

MINE 112 uses the knowledge available from existing medical terminologies and combines it with knowledge extracted using sophisticated semantic analysis techniques to provide health care providers the critical ability to access relevant information instantly at the point of care.

Healthcare reform has brought about initiatives such as accountable care, sustainable health and shared savings. Participating organizations are challenged to decrease cost of care, measure population health, improve quality and demonstrate meaningful use. To comply, they need to effectively leverage ALL their data whether that information exists within provider offices, acute care settings, or billing systems. Using data is further challenged since approximately two-thirds or more of the key clinical information is typically found in free text notes and scanned documents, which are inaccessible and unusable by today's healthcare technology solutions.

Healthcare organizations can use MINE 112 as their data foundation to aggregate and unlock the full potential of their coded and unstructured data from across multiple sites. Clinical Knowledge Exchange (CKX) CKXREF approaches healthcare information exchange (HIE) with AI-based processing. Typically, an HIE needs to go beyond exchange of standard data to deliver actionable information. Accordingly, the CKX CKXREF Data Interface 113 is capable of importing data in many formats. Further, MINE 112 can include a Reconciliation and Deduplication Module for reconciling the imported data, and MINE 112 can also include an Indexing and Meta Tagging Module for tagging the imported data in a manner that makes the information ready for viewing and analysis. Hence, MINE 112 permits the use of coded data such as template entries and claims data, and also makes useful unstructured data found in clinical narrative. If the clinical narrative is in scanned documents, CKX CKXREF automatically extracts the textual information using Optical Character Recognition (OCR). The post processed and original data can be stored in a High Performance Data Storage unit(s), locally or distributed, resulting in queryable and computable with sub-second response.

CKX CKXREF can also interoperate with EHRs, HIEs, PACS, Quality and Billing Systems. For example, MINE 112 can receive and process many types of data from EHRs and PMs including coded data, textual and image-based documents by leveraging a combination of proprietary and standard data interfaces. Standard data interfaces supported include CCD, CCR, C32, X.12 and HL7 V2. MINE 112 can also supports HL7 V2 and IHE XDS, IHE XDR protocols for hospital and enterprise level integration.

In addition, MINE 112 can also inter-operate with any application and bi-directionally exchange clinical information using the API APIREF.

Data Security and Privacy

Data Security and Privacy can also be integral to MINE 112. To ensure data security and privacy, MINE 112 applies best practice standards and technology in data encryption. For example, to ensure HIPAA compliance, MINE 112 limits clinical record access to only members of a patient's care team. Others not on the patient's care team, such as in case of urgent care providers, can gain immediate access to the patient record by "breaking the glass". These transactions can be tracked and be fully reportable.

The data exchange module 117 may transmit and receive data in using industry standard SSL connections and all Protected Health Information (PHI) may be encrypted. Module 117 can also maintain detailed audit logs for all applications and users accessing data. The secure data access is optimized for web-browser viewing on most platforms including Windows, Macintosh, Unix, Linux, iPad, iPhone, Android, and Blackberry.

Data Consistency

Many patients, especially older individuals with many chronic diseases, seek care from by multiple healthcare providers working in separate and diverse environments, including private practices, group practices, and hospitals. Each of these sources generates data to describe and code the patient's medical information differently, and will eventually create a distinct continuity of care document for each encounter. The MINE 112 can analyze the patient's entire record, organize it, and present it to the healthcare provider in a format that can be efficiently viewed and interpreted. Reconciliation and de-duplication of data are performed dynamically by the Reconciliation & Deduplication Module for presentation using Presentation & Quality Checking Module, while data is also kept in its original form, without data loss.

Master Patient Index

MINE 112 can also include an Enterprise Master Patient Index technology (EMPI) EMPIREF. MINE 112 can use an existing EMPI or leverage IHE PIX/PDQ standard or operate independently. This EMPI can operate in two different modes: (1) Automatically find matching patients based on organization specific rules or (2) the Presentation & Quality Checking Module of MINE 112 enables users to identify potential matches and merge records on-demand. MINE 112 can keep track of all patient merges and allow users to un-merge records in case of an error. The Indexing & Meta Tagging Module of MINE 112 can also include fuzzy match algorithms that can be used for population analysis.

Application Programming Interface (API)

For software application vendors providing EHR, HIE, PHR, PACS, home monitoring, or medical devices, and those who are developing novel health applications, the system API APIREF offers the unique ability to exchange data with the Clinical Knowledge Exchange CKXREF platform using a SOAP API APIREF. The medically intelligent search solution can also be embedded inside an application using a REST API APIREF.

Examples of sections and vocabularies supported by MINE 112 include Problems (free text, ICD9 codes), Office Notes (full, adhoc text in CCD), Medications (free text, RxNorm codes), Allergies (free text), Labs (free text, CPT codes), Procedures (free text), and Immunizations (free text).

In some embodiments, the MINE 112 system may also interoperate many other systems, including EHRs, HIEs, PACS, Quality and Billing Systems.

Population Analyzer

In some embodiments, MINE 112 also includes a Population Analyzer that provides an on-demand and flexible solution for clinicians, care managers, and administrators to efficiently manage a group of patients and better target interventions to achieve better care experiences and population health improvement. This tool is an essential dashboard to help guide a performance-driven organization to meet clinical and financial objectives.

Using the latest advances in big data science, the MINE Population Analyzer can provide in real-time very accurate views of a patient population at multiple levels, including but not limited to:

a. disease and condition registries
b. patient risk stratification (e.g., co-morbidities)
c. quality measure compliance (e.g., Medicare PQRS and ACO measures)
d. patient-level actionable care gaps (e.g., diabetics who need retinal eye exams)
e. clinical questions answered using intelligent population search The MINE Population Analyzer can intelligently mine and extract relevant data from the clinical narrative to enrich existing coded data, all of which may be aggregated from multiple data sources. This greatly improves condition identification, measure reporting, risk assessment and other clinical analyses. The Population Analyzer results can be viewed according to the type of data used in the analysis: coded data only versus coded data plus information mined from textual data. With Population Analyzer, there is no need to create custom, costly, and time-intensive reporting views or cubes.

The MINE Population Analyzer may be directly accessed within many clinical management platforms or electronic records via MINE 112 application interfaces 113 and 117. Furthermore, the data and results can be queried by quality reporting and decision support systems.

The MINE population analyzer enables the user to request (via text query, API call, GUI, and other interfaces) aggregated statistical information for a specific cohort of patients, computed from structured data only AND computed from a combination of structured and unstructured data.

Such information includes, but is not limited to, #males, #females, #diabetics, #(other conditions of interest), numerator, denominator and % compliance for specific measures of interest (e.g., PQRS, CORE, ACO 33, HEDIS, etc.)

A cohort can be any set of patients. Some cohorts of specific interest are patients enrolled in an ACO or other care management organization, patients seen within an organization, patients seen by a particular provider, patients seen by a particular specialty within an organization, patients covered by a particular health plan, insurance or plan type. Many other cohorts can also be of interest.

Any group of patients that comprise a result value in a page of results (e.g. organization results, provider results, etc.) is a "Result Cohort." The minimum cohort displays will be by organization and by provider.

MINE Population Analyzer can also enable the user to "drill down" to a page of specific results for each patient in a cohort or result set. Patient-level results shall include results (facts) for specific clinical measures (e.g., PQRS, CORE, HEDIS, ACO 33, etc.), and specific documents and information sources that were used to infer results or facts about the patient.

Accordingly, the MINE Population Analyzer may include one or more of the following capabilities:

a) scalable system to process large amounts of data and store it into the patient model.
b) The ability to quickly query across the data for known use-cases (e.g., query by problems, pairs of problems, etc.).
c) A usable system that supports SQL like queries so non-technical users can use the system (select, project and aggregate functionality).
d) Usable from Pig 0.9.2 (release version of this document, 0.10 is out, but it is not yet in "stable" branch).
e) Both streaming/in-memory access to the data.
f) AES compatible encryption can be supported from the Get-Go, no excuses.
g) Pig 0.9.2 schema types (i.e., schema as enforced by pig).
h) Blobs in the dataset can be represented as SortedSpillableDataBag with a tuple having the following chunk information (offset, chunkdata (up to 1 MB), checksum).
i) Immutable column families (because alter table is a map-reduce job away).
j) Metadata can be stored in the TFile metadata block.
k) Writes can be lock-free and resort to anti-entropy mechanism (maybe lamport timestamps/vector clocks/version clocks).
l) Replication, high-availability etc. can be handled by hadoop.

m) Backups are distcp to s3 (no incremental backups, but we can have rolling backups, etc. but they are all cron jobs outside of the system).
n) Each value tuple can have the following information:
Row key (BYTEARRAY)
Format Version (INTEGER)
Version (LONG) (used in read-repair scenarios)
Writer Timestamp (LONG)—(timestamp, as seen by the writer in _seconds_)
Active (INTEGER) (0/1) value indicating if
A sequence of values which is in-of-itself another tuple (TUPLE, matching the schema in the metadata block).
Any blobs can be represented as a sorted spillable databag with an internal chunked encoding.
o) The key it the tfile can be MD5 of the key itself
p) The metadata block of the TFile can include an index over the keys (so we load the first metdata block and load data files from it).
q) Since TFiles are immutable, "merge" or grim-reaper jobs can be required including performing read-repair.
r) Realtime Reads can happen through a service that loads the metadata block into an in-memory array and indexes into the t-file (include random network reads, but good caching should make this problem relatively easier).
s) Realtime writes happen by updating the metadata block and a corresponding commit log (which is a file that is written to hadoop and flushed immediately).

Muir ACO. PQRS

|  | | Males | | Females |
|---|---|---|---|---|
| # of patients | xxx | xxx | | xxx |

|  | Coded | Text + Coded |
|---|---|---|
| # of diabetics | xxx | yyy |
| # of HF | xxx | yyy |
| # of CAD | xxx | yyy |
| # of COPD | xxx | yyy |
| # of HTN | xxx | yyy |

|  | Coded data | | | Coded + Text | | |
|---|---|---|---|---|---|---|
| Measure | num | denom | % comp | num | denom | % comp |
| diabetes with retinal eye exam | 10 | 100 | 10% | 10 | 100 | 10% |
| diabetes with foot exam | 15 | 300 | 5% | 15 | 300 | 5% |
| HF with LV eval | 20 | 100 | 20% | 20 | 100 | 20% |

Search Term: Dr Smith PQRS

|  | | Males | | Females |
|---|---|---|---|---|
| # of patients | xxx | xxx | | xxx |

|  | Coded | Text + Coded |
|---|---|---|
| # of diabetics | xxx | yyy |
| # of HF | xxx | yyy |
| # of CAD | xxx | yyy |
| # of COPD | xxx | yyy |
| # of HTN | xxx | yyy |

|  | Coded data | | | Coded data + Text | | | |
|---|---|---|---|---|---|---|---|
| Measure | nun | denom | % comp | num | denom | % comp | Health System |
| diabetes with retinal eye exam | 1 | 5 | 20% | 1 | 5 | 20% | |
| diabetes with foot exam | 3 | 10 | 10% | 3 | 10 | 10% | |

Search Term: John Sample PQRS

| Measure | Numerator |
|---|---|
| diabetes with retinal eye exam | NO |
| diabetes with foot exam | YES |
| HF wth LV assessment | NO |

(click on the measure and get the set of measure facts)

| Measure | Measure Facts | Source | Date |
|---|---|---|---|
| diabetes with foot exam | Diabetes | Claims | Jan. 1, 2012 |
| diabetes with foot exam | Foot exam | Doc | Feb. 12, 2012 |
| diabetes with foot exam | Foot exam | Doc | Jan. 12, 2011 |
| diabetes with foot exam | Foot exam | Doc | Nov. 12, 2011 |
| diabetes with foot exam | PCOS | none | na |

Quality Optimizer QMREF

The analysis of care quality within any healthcare organization begins with understanding how well patients are being treated according to evidence-based care measures. These results become the basis for managing populations, targeting patient interventions, and profiling physician performance. It is difficult to manage what cannot be readily measured. For many organizations, the process of quality analysis can be time-consuming and costly and often inaccurate.

As discussed above, approximately two-thirds or more of the data useful for quality measure sets in common use (e.g., Medicare ACO, PQRS, and HEDIS) is typically found in free text notes and scanned documents. This narrative information cannot be easily processed by quality reporting tools in use today. In addition, the relevant data may be located in multiple systems across an organization. As a result, these tools may under-estimate performance or include ineligible patients into reporting and analysis, decreasing overall accuracy.

The MINE 112 can aggregate clinical and billing data from multiple systems within an organization. MINE 112 can intelligently mine both discrete and textual data in an automated fashion for relevant quality measure concepts. MINE 112 can apply terminology codes for relevant data found within the clinical narrative. MINE 112 can export information to most quality tools including GPRO using application interfaces 113 and 117. MINE 112 can expose a validation tool for clinicians and others to view source documentation from which relevant concepts were found (e.g., diabetic foot exam).

It can be demonstrated that as much as a two-fold improvement in patient compliance with quality measures such as diabetic kidney disease screening could be achieved by simply including data mined from the clinical narrative in the measure calculation. There was no change in clinical workflow or care delivery.

Figure 2:
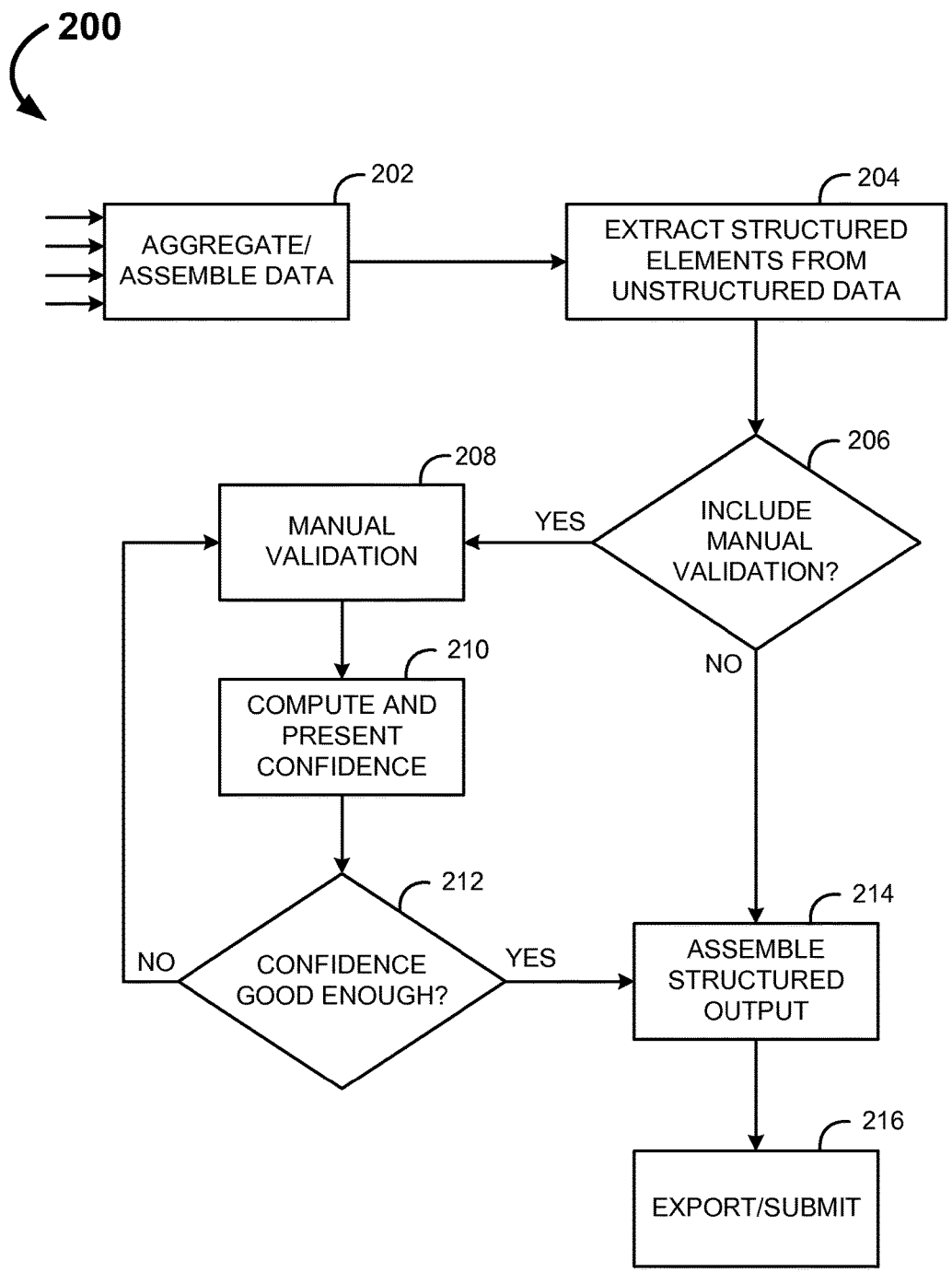
FIG. 2 is a flow diagram illustrating how data can be aggregated, assembled and confidence level computed for the MINE 112 of FIG. 1.

The MINE Quality Optimizer QMREF more accurately uncovers services completed for a patient in an automated fashion without the need for a costly chart review. In addition, a healthcare organization could potentially gain more revenue where measure performance is tied to reimbursement as illustrated by the flow diagram of FIG. 2.

In step 202, data is aggregated by the MINE QMREF. Text is structured with concepts relevant to quality measurement (diseases, procedures, measurements, etc.) in step 204. If manual validation is required, then the output is validated (see steps 206, 208). In step 210, the confidence of the measure value is computed and presented. The validation and confidence computation steps can be repeated as needed (steps 212, 208, 210).

If manual validation is not required (step 206), or if the confidence is acceptable, then structured data and extracted structure can be combined (into structured output (can be standard type)) (see steps 206, 212, 214). The results are available for reporting/submit step if appropriate (step 216).

Presentation of Confidence

In some embodiments, confidence level translates into a lower bound on the probability that a reported outcome (e.g., a measure numerator) is >=the actual outcome. Actual outcome is the value that would be determined in a complete manual audit (a.k.a. 100% audit).

Figure 3:
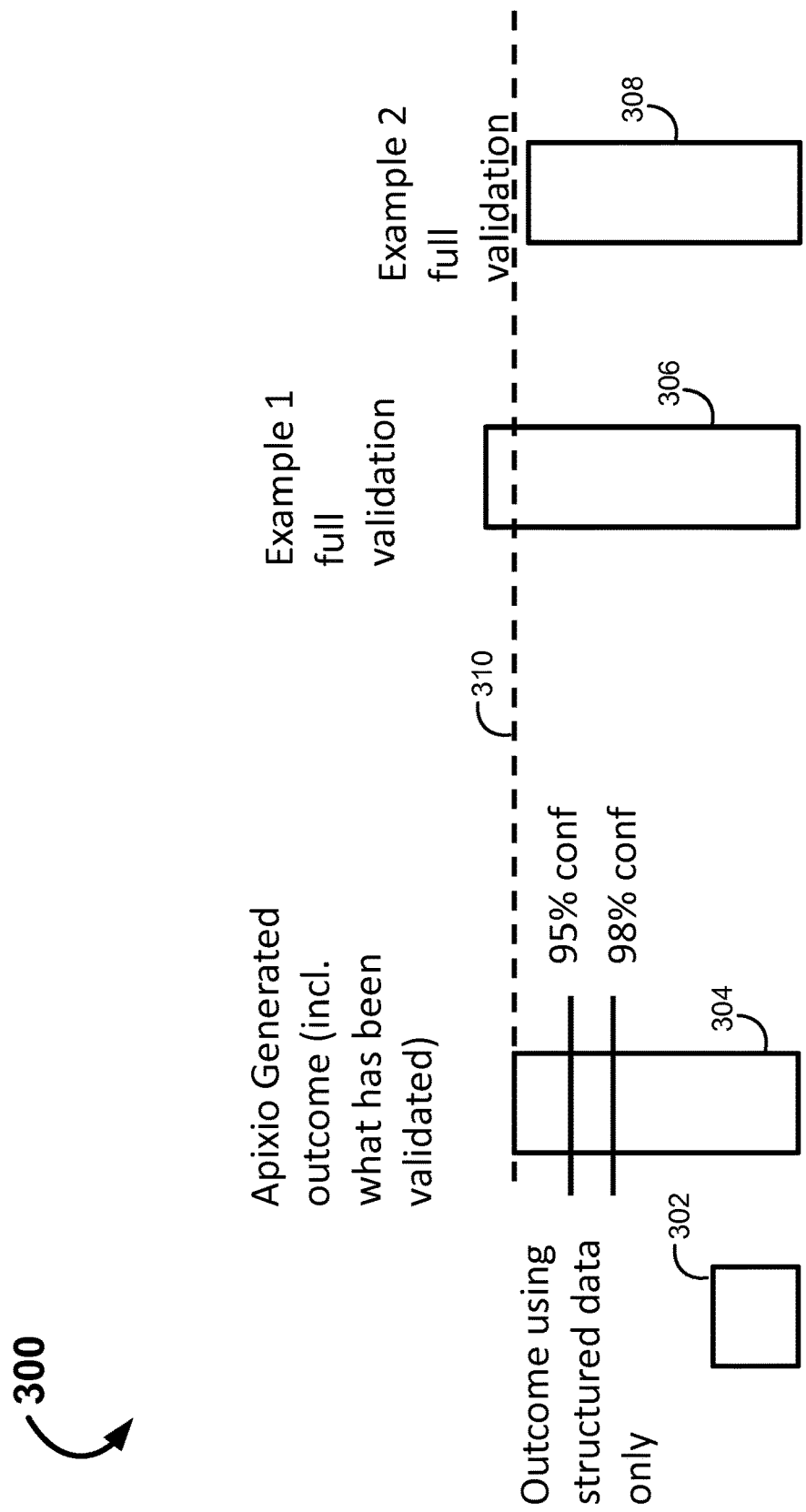
FIGS. 3 and 4 illustrate exemplary outcome validations for the MINE 112 of FIG. 1.
Figure 4:
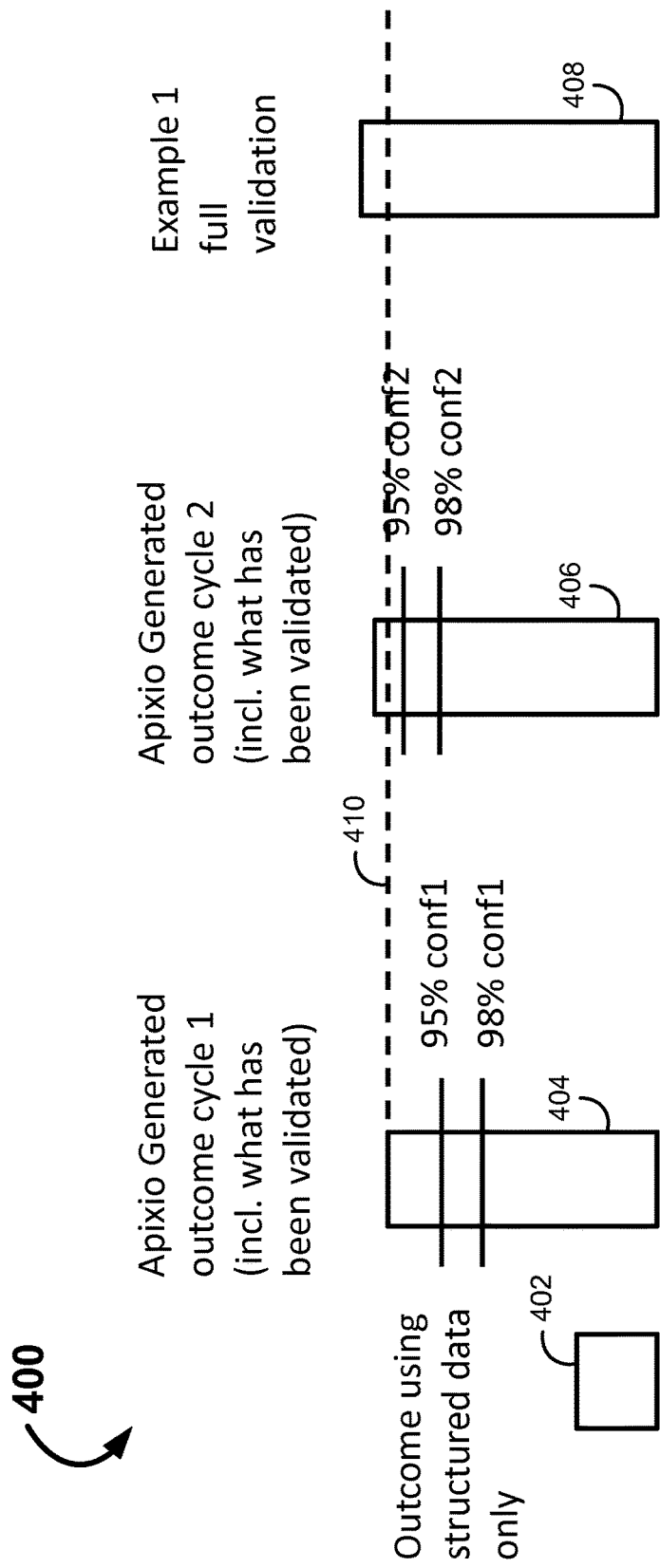

What is presented to the user is the value computed by the algorithm output adjusted by any validated results ("generated outcome") and the outcome value that corresponds to a specific confidence level. For example, as illustrated by FIGS. 3 and 4, the user may set the confidence level to a specific value, such as 95%, and see the outcome that this corresponds to.

Computation of Outcomes Corresponding to Various Confidence Levels

In an exemplary computation: Assume 100% audit yields an outcome p (expressed as a rate from 0-1). Then Hoeffding's inequality gives the equation:

$$Pr(\epsilon,n) \leq e^{-2\epsilon^2 n}$$

where $\epsilon$ is difference in measured rate from p, and
n is number of included patients.
Set $Pr(\epsilon,n)$ to 0.05 for 95% confidence level, put in n (the number of patients tested for outcome) and solve for 6 to get outcome value corresponding to confidence level.

Other embodiments account for systematic errors which are introduced when precision and recall are less than 100%.

HCC Optimizer HCCREF

In some embodiments, MINE 112 also includes a subsystem HCC Optimizer HCCREF that enables healthcare organizations and their health plan affiliates to optimize reimbursement revenue for their Medicare Advantage members. HCCREF does so by automatically identifying and presenting coding opportunities where it finds gaps between clinical documentation and claims data for members in a reimbursement year. HCC Optimizer module HCCREF can be powered by the Clinical Knowledge Exchange (CKX) CKXREF. HCC Optimizer HCCREF therefore can aggregate data from multiple sources and included unstructured data from free text, scanned documents and clinical narrative.

Workflow Overview

In some embodiments, HCC Optimizer HCCREF finds compliant revenue opportunities and therefore can, as a result, reduce costly overhead for manual chart audits. The HCC Optimizer tool is very efficient and easy to use, requiring little training HCC Optimizer may also assist coders identify, verify source documentation and select optimal ICD9 codes in the follow three exemplary steps:

1. Automatically identifies coding opportunities based on conditions found in unstructured clinical data but not noted in a claim and presents them as a focused list.

2. A certified coder with one click can pull up and review the source document(s) and verify the clinical evidence.

3. Coder is presented with and can select from a targeted and highly optimized set of ICD9 codes. The resulting list of new codes can be exported, printed or entered into a billing system.

The solution can also be used as an internal auditing tool to reduce exposure to a CMS audit by identifying diagnosis codes billed for, but not supported in, clinical documentation.

Filling Information Gaps with Actionable Knowledge

In some embodiment, the Clinical Knowledge Exchange (CKX) CKXREF can also assist healthcare organizations fill the information and intelligence gaps created by disparate and poorly connected computer systems across a provider community. CKX CKXREF enables these organizations to improve the quality of patient care while lowering costs and optimizing reimbursements.

CKX CKXREF can integrate electronic data, both structured and unstructured, from across an entire healthcare organization. By mapping and reconciling the integrated patient data, MINE 112 makes data accessible and actionable by clinical staff and mission critical systems.

Health Systems & ACOs

It should be appreciated that there are many different models of accountable care being developed in healthcare organizations today. Whether you are a full Pioneer ACO, MSSP, gain share, risk share or simply setting up a clinically integrated institution you will need access to data. Organizations are challenged to decrease cost of care, measure population health, improve quality and demonstrate meaningful use. Healthcare facilities need access to ALL data whether that information exists within provider offices, billing systems, acute care systems or in partnerships with other organizations.

Since approximately two-thirds of the information required for these measures is found in free text notes and scanned documents, which are inaccessible by most healthcare technology solutions today. In addition, organizations need to aggregate patient data from multiple information systems which further complicates their reporting requirements. One cannot manage what one cannot measure.

The Clinical Knowledge Exchange CKXREF takes data from multiple sources in an organization, and maps it together, including physicians that are still not automated, as we include scanned documentation. The system not only makes use of coded data such as template entries and claims data, but also unstructured data found in scanned documentation and clinical narrative. The technology of CKX CKXREF uses innovative approaches such as optical character recognition, natural language processing, and machine learning on a cloud-based, scalable platform.

Examples of ACO applications include foundation for data aggregation and analysis; unlock the full potential of data using Natural Language Processing; optimize quality measures using ALL data, and optimize care management by generating accurate worklists.

Medicare Advantage Plan Providers

Medicare Advantage reimbursement depends on number and severity of conditions for a given patient in a given year. Often physicians enter a patient's condition in the progress note and not code it with ICD9. This lack of coded information can significantly reduce the ability of a healthcare organization and its affiliated health plan to be properly reimbursed.

Utilizing the latest advancements in natural language processing and data mining, CKX CKXREF automatically identifies gaps between coded claims data and physician narrative data found in free text, documents and images. The system then presents a list of coding opportunities, source documents containing the clinical evidence and optimal set of ICD9s to a certified coder for review and verification. The suggested codes once verified by a coder, increasing Risk Adjustment Factor (RAF) for the member in accordance with regulations provided for HCC coding. Additionally, the CKX CKXREF can also be used as an internal auditing tool to reduce exposure to a CMS audit by identifying diagnosis codes claimed for reimbursement but not supported in clinical documentation.

Medical Groups & IPAs

Physician groups take on many shapes and sizes from MSOs to IPAs to a self-owned, self-governed provider organization. Although Accountable care organizations take up only seven pages of the extensive Affordable Care Act, it has become one of the most talked about provisions. No matter how a physician organization defines itself the words accountable care or sustainable health are most likely being spoken in break rooms and board rooms alike. The challenge is where does one begin? Phrases like gain share, pay for performance, and Medicare Shared Savings Programs are continually bantered about. Provider organizations that have been taking risk for years are most likely continuing to do so and will again most likely take on a bigger initial portion of accountable care. Provider organizations that have not traditionally had a risk model for patient populations will most likely start with a toe or a foot in the accountable care ocean.

No matter which sustainable health or accountable care model an organization decides to undertake—they all need one foundational item. In order to manage the health, quality and cost of a population of patients, the organization must have access to ALL data pertinent to that population. One cannot manage what one cannot measure.

For example, if an organization has only one single EHR, then the organization is likely to have multiple years of data that is not accessible within that system or is cumbersome to find. If the organization is an IPA or a larger organization you may have multiple EHRs or even physicians still operating on paper. Studies have shown that approximately two-thirds of clinical data is found in unstructured format: free text entries, progress notes, dictation and scanned documentation. This narrative information, which is unstructured, cannot be used by reporting tools in use today. In addition, the relevant data may be located in multiple systems across an organization. As a result, these tools may under-estimate performance or include ineligible patients into the analysis, decreasing overall accuracy.

Independent Clinics

Independent clinics and specialty practices often do not have all the expertise and resources to deal today's complex IT environment and as a result the patient data is often fragmented across different systems and sites. These interoperability and data sharing challenges often result in inefficient use of physician and personnel time and unfortunately at times creating undue clinical risk.

The CKX (Clinical-knowledge Exchange) platform CKXREF provides a solution for independent clinics that need to resolve their data aggregation, mobility and sharing problems.

Patient medical history is uploaded by the Interface 113, Indexing & Meta Tagging 16 is performed for all medically relevant patient historical information using MATRIX 105, which may include four million or more medically coded concepts.

MINE 112 allows medically intelligent search to be performed on a patient's history.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A method for improving reporting of recognized Medicare Accountable Care Organization (ACO) quality measures performed by a medical information navigation engine (MINE), useful in association with at least one electronic health record (EHR) system, the method comprising:
   aggregating clinical data and billing data from at least one electronic health record system, wherein the clinical data includes medical records, healthcare device generated information, information entered by a patient, text information entered by a care provider, and scanned documents;

extracting concepts within the clinical data using a database of medical concepts and relationships between the medical concepts;

identifying at least one ACO quality measure using the extracted concepts;

determining a measured quantity of the identified at least one ACO quality measure;

receiving a probability rate of an ACO quality measure being found by a complete manual audit;

determining a number of patients in the at least one electronic health record system;

calculating an expected quantity of ACO quality measure being found by the complete manual audit by multiplying the probability rate by the number of patients;

subtracting the measured quantity from the expected quantity to generate a variable;

solve a confidence level for the variable using the number of patients and Hoeffding's inequality equation;

receiving an acceptable value for the confidence level;

comparing the confidence level to the acceptable value; and exporting the at least one recognized ACO quality measure identified using the extracted concepts for reporting or for manual validation responsive to the confidence level meeting the acceptable value.

2. The method of claim 1 further comprising providing a validation tool for users, including clinicians, to search and view clinical data.

3. The method of claim 1, further comprising applying terminology codes to the extracted concepts.

4. The method of claim 1, wherein the exporting is through an application interface.

5. The method of claim 4, wherein the exporting is to a GPRO quality tool.

6. The method of claim 1, further comprising updating the identified at least one ACO quality measure with validated results.

7. The method of claim 6, further comprising repeating the calculation of the confidence level using the updated identified at least one ACO quality measure.

8. The method of claim 1, further comprising receiving a listing of codes associated with the at least one electronic health record system.

9. The method of claim 8, further comprising identifying which of the extracted concepts are not reflected in the listing of codes associated with the at least one electronic health record system.

10. The method of claim 9, further comprising recommending the identified extracted concepts that are not reflected as reimbursement opportunities.

* * * * *